United States Patent [19]

Keller et al.

[11] Patent Number: 5,102,711
[45] Date of Patent: Apr. 7, 1992

[54] BREATHABLE LAYERED MATERIALS

[75] Inventors: Mary L. Keller, Newark, Del.; Peter Brown, Elkton, Md.

[73] Assignee: W. L. Gore & Associates, Inc., Newark, Del.

[21] Appl. No.: 505,295

[22] Filed: Apr. 5, 1990

Related U.S. Application Data

[63] Continuation-in-part of PCT/US88/03997, Nov. 7, 1988, which is a continuation-in-part of Ser. No. 120,330, Nov. 13, 1987, Pat. No. 4,816,328.

[51] Int. Cl.[5] .................. A41D 31/02; A61F 5/04; A61F 13/46; A61F 13/50; B32B 3/06
[52] U.S. Cl. ..................... 428/71; 2/243 R; 428/74; 428/76; 428/157; 428/159; 428/169; 428/315.9; 428/316.6; 428/422; 604/369; 604/372; 604/378; 604/385.1
[58] Field of Search ............... 128/83, 89 R; 428/71, 428/74, 76, 315.9, 157, 159, 169, 316.6; 604/369, 372, 378, 385.1; 2/243

[56] References Cited

U.S. PATENT DOCUMENTS

| 4,235,228 | 11/1980 | Gaylord, Jr. et al. |
| 4,433,026 | 2/1984 | Molde |
| 4,532,316 | 7/1985 | Henn |
| 4,622,036 | 11/1986 | Goodrum ........... 428/315.9 |
| 4,645,698 | 2/1987 | Matsubara ........... 428/74 |
| 4,690,847 | 9/1987 | Lassiter et al. ........... 428/71 |
| 4,807,303 | 2/1989 | Mann et al. ........... 428/71 |
| 4,816,328 | 3/1989 | Saville et al. |
| 4,902,565 | 2/1990 | Brook ........... 428/315.9 |
| 4,957,795 | 9/1990 | Riedel ........... 428/74 |

FOREIGN PATENT DOCUMENTS

| 0123965 | 11/1984 | European Pat. Off. |
| 0160473 | 11/1985 | European Pat. Off. |
| 2737756 | 3/1979 | Fed. Rep. of Germany |
| 61-12367 | 5/1986 | Japan |

Primary Examiner—James C. Cannon
Attorney, Agent, or Firm—Gary A. Samuels

[57] ABSTRACT

A flexible, breathable, non-linting, composite is provided. The laminate comprises a middle layer of a padding and a top and bottom layer comprising a sheet of porous water impermeable, moisture-vapor-permeable film bonded to the middle layer. Preferably the top and bottom layers comprise (a) a flexible, first sheet of hydrophobic material having a moisture vapor transmission rate exceeding 1000 gms./m$^2$·day; and (b) a continuous hydrophilic sheet attached to or penetrating the first sheet, the hydrophilic sheet having a moisture vapor transmission rate exceeding 1000 gms./m$^2$·day and forming a barrier to passage of fluids. The composite is useful in diverse applications such as a padding under orthopedic casts and as thermal insulation in wearing apparel.

12 Claims, 1 Drawing Sheet

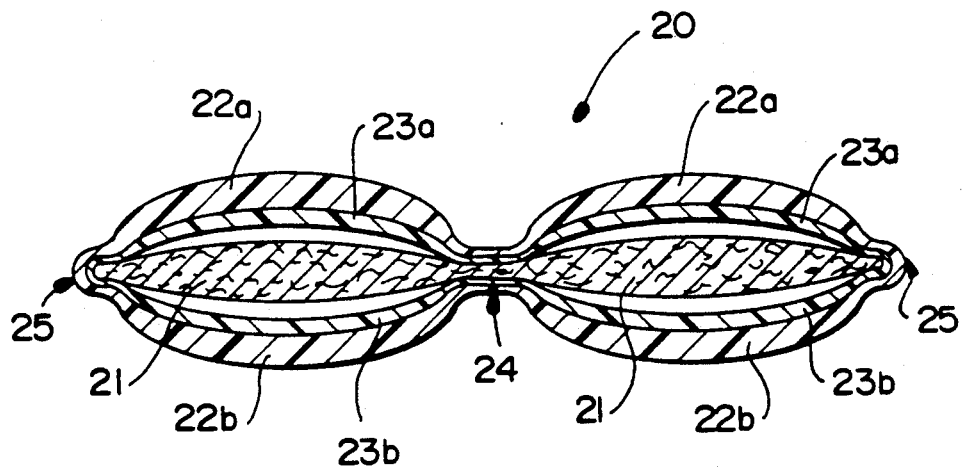
Fig. 1
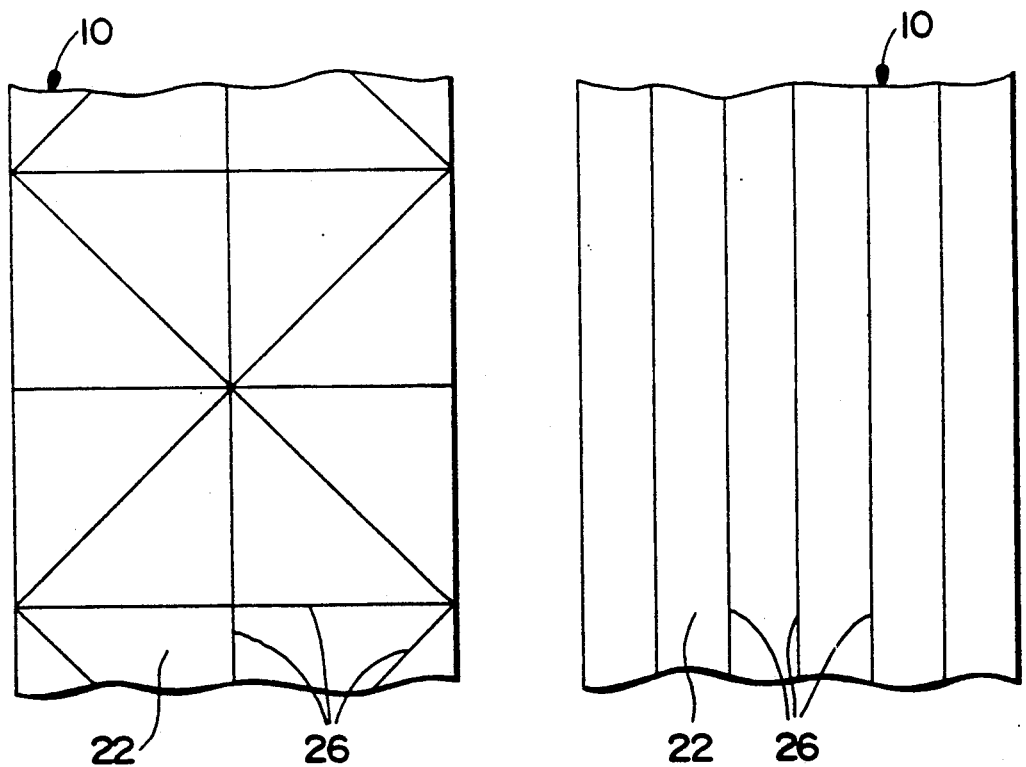
Fig. 2
Fig. 3

BREATHABLE LAYERED MATERIALS

CROSS-REFERENCE TO RELATED APPLICATION

This application is a continuation-in-part of PCT Application Ser. No. PCT/US88/003997, filed Nov. 7, 1988, which is a continuation-in-part of U.S. patent application Ser. No. 07/120,330, filed Nov. 13, 1987, now U.S. Pat. No. 4,816,328.

FIELD OF THE INVENTION

This invention relates to a layered composite of a padding between two layers of water impermeable, moisture-vapor-permeable porous film, preferably porous, expanded polytetrafluoroethylene, useful, inter alia, as padding underneath orthopedic casts and braces and as thermal insulation in wearing apparel. The layers of porous film surrounding the padding protect the padding, especially in applications where the padding is ordinarily susceptible to becoming wet.

BACKGROUND OF THE INVENTION

Fabrics used for underpadding for limb casts have included cotton, foams, synthetics such as polyester fiberfill and wool. The major functions of underpadding are cushioning, filling and thermal insulation. Medical uses for paddings include applying or relieving pressure and absorption of excess moisture. Most currently available underpaddings lose some of their functionality when immersed in water. Hater can cause padding to compress or to shift due to weight gain. It also alters the insulating properties of most paddings and can cause extreme discomfort. In addition, a water-saturated underpadding is not useful for transfer of moisture away from the skin. This loss of function is especially critical when the padding is worn by a person for extended periods. Prolonged wetness next to the skin causes skin breakdown and possible infection sites. It is therefore desirable to provide a padding which will not be adversely affected by exposure to water. It is also desirable to provide padding that will allow the transfer of water vapors so that perspiration and other body fluids can escape.

In the past, several methods have been used to overcome some of the drawbacks of padding. Quilting has been used to prevent padding from shifting, while maintaining high loft and bulkiness desirable in padding. Bonding padding to a fabric backing also prevents shifting. Fiberfill consists of crimped fibers to help maintain fluffiness and air space, even upon exposure to water. Hollow fibers also contain air space which add insulating value. Synthetic fibers are generally less absorbent than natural ones and have been used to wick fluids away from the skin into more absorbent backings. However, fluid saturation results in loss of function.

Large quantities of padding are used under immobilizing orthopedic casts or braces. Traditional cast underpadding consists of cotton or polyester wraps in 2 inch to 6 inch widths. Care is taken when applying the underpadding to avoid folds or creases which can cause pressure sores to the skin. The immobilizing material applied on top of this padding is usually made of plaster of paris or polyurethane-coated fiberglass. Cast wearers are usually told not to immerse the cast in water, even though polyurethane casts can withstand water immersion. If a traditionally padded polyurethane cast is immersed, the padding remains wet for many hours, and the result can be skin maceration. In some cases, this maceration can lead to skin breakdown and infection by bacteria or fungi. Cast padding material manufacturers often caution against water immersion and state that if a cast is wet, it should be completely dried with a hair dryer. This drying process can take several hours and patient compliance is extremely low. Some cast wearers use plastic bags with rubber bands around the end to keep water away from the cast while showering. Hater often enters the bag and wets the padding which causes discomfort to the wearer. As a result, many cast wearers do not want to get their cast wet and spend the time they are wearing a cast without a normal shower or bath. In addition, cast wearers cannot swim or use any form of hydrotherapy.

It is widely recognized that paddings must be "breathable" to be comfortable. However, it is not necessary that air pass through the padding for it to be comfortable, only that water vapor from perspiration or other sources be transmitted from the skin outwards through the padding. "Breathability" and the ability to transport interior moisture vapor to the external environment are used interchangeably herein.

As used herein, the term "porous, expanded polytetrafluoroethylene" is as disclosed in U.S. Pat. No. 3,953,566. The term "breathable" as used herein means the ability to transport moisture from the humid side of a hydrophilic member and discharge the moisture on the dry side of the member, as disclosed in U.S. Pat. No. 4,194,041. Both of these patents are assigned to assignee herein and both are incorporated here by reference thereto. The terms quilt, quilted and quilting refer to a pattern of discretely-shaped cells.

SUMMARY OF THE INVENTION

A flexible, breathable, non-linting, composite is provided comprising a middle layer of a padding and a top and bottom layer of water-impermeable and moisture-vapor-permeable porous, expanded polytetrafluoroethylene. The top and bottom layer each preferably comprise a flexible, first member of hydrophobic material having a moisture vapor transmission rate exceeding 1000 gms./m$^2$ · day. A continuous hydrophilic member may be joined with, i.e., attached to or penetrate the pores of the first member, the hydrophilic member having a moisture vapor trasmission rate exceeding 1000 gms./m$^2$ · day and forming a barrier to liquids. The middle layer may be a synthetic material such as polyamide, polyester or polybenzimidazole fabric, woven, knitted or non-woven. It may comprise natural fabrics such as cellulosics or wool, or may be made of down. The middle layer may alternatively be a foam, a glass cloth, glass mat or any fabric of organic or inorganic fiber.

BRIEF DESCRIPTION OF THE DRAWINGS

FIG. 1 is a perspective view, partly in cross-section, of a composite according to the invention.

FIG. 2 is a top plan view of one embodiment of a quilted composite according to the invention.

FIG. 3 is a top plan view of an alternate embodiment of a quilted composite according to the invention.

DETAILED DESCRIPTION OF THE INVENTION

A flexible, breathable, non-linting layered composite is provided. The composite comprises a middle layer of a padding preferably a polyamide, polyester or glass fabric, and preferably being non-flammable, and a top and bottom layer of water impermeable and moisture-vapor-permeable film. Preferably a film of porous expanded polytetrafluoroethylene is bonded to the middle layer around the edges as described in the Example. Preferably the top and bottom layers comprise a flexible, first member of hydrophobic material having a moisture vapor transmission rate exceeding 1000 gms./m$^2$ · day. A continuous hydrophilic member may be joined with the first member, the hydrophilic member having a moisture vapor transmission rate exceeding 1000 gms./m$^2$ · day and forming a barrier to passage of liquids where the hydrophobic members are both external to the middle layer.

The composite is useful in such diverse applications as a padded liner under orthopedic casts and braces and as an insulation in wearing apparel.

A detailed description of the invention and preferred embodiments is best provided with reference to the drawings.

FIG. 1 depicts a cross section of the embodiment of the invention described in Example 1. The protective padding 20 comprises a middle layer of padding material 21 and could be in woven, non-woven or knit form, and top outer protective layer 22a and bottom outer protective layer 22b each made of a sheet of water-impermeable, water vapor-permeable material (which is porous, expanded polytetrafluoroethylene film) and each of which is coated with hydrophilic impregnant 23a and 23b (which is hydrophilic breathable polyurethane). The top and bottom outer protective layers are bonded to the middle layer 21 at quilt bond point 24 by simply thermally sealing the materials together, and at outer periphery bond seams 25. The coated water-impermeable, water vapor-permeable top and bottom outer protective layers and the middle layer are not bonded or attached to each other at any other points.

FIG. 2 is a top plan view of a quilted embodiment 10 of padded liner for use in an orthopedic cast according to the invention, wherein the quilted pattern is in the form of triangles bounded by quilt lines 26. FIG. 3 is an alternate embodiment having parallel quilt lines 26. Protective layer 22 is a sheet of water-impermeable water vapor-permeable material.

For use as a padded liner under a cast, it is desirable to divide the composite into smaller units or cells through quilting or embossing. This is useful not only to prevent shifting but also to protect each cell from water which may enter through a hole or defect in adjacent cells. This will allow the quilted composite to be cut or trimmed without violating the integrity of the whole pad.

The quilted composite can be manufactured by sealing the edges of the cells to completely encompass the padding. This sealing can be done in many ways, for example using direct heat or ultrasonic welding or adhesives.

When the composite is used as a padded liner in cast, the outer layers do not allow liquid water to pass through to the inner layers. However, water will pass through the film after it has been vaporized. Additionally, the body heat of the wearer causes this evaporation process to occur and creates a one-way path for water vapor. If the padding becomes moist, the moisture is still directed outwardly through the case, not back towards the person. Therefore, padding encapsulated in quilted composites of this invention does not experience the same water weight gain that unprotected underpadding does and the wearer does not have to wait as long to experience dryness. The skin surface dries much faster with the breathable composite laminates of this invention than with unprotected underpadding. Perspiration is allowed to pass through the beathable composites without moisture remaining on the skin. Traditional underpadding remains damp for many hours, but the padding in composites of this invention dries quickly. This provides the wearer with a great deal of comfort.

A number of commercially available materials are suitable for use as the water impermeable, moisture-vapor-permeable, porous film. These materials include microporous expanded polytetrafluoroethylene as described in U.S. Pat. Nos. 3,953,566 and 4,187,390; and expanded polytetrafluoroethylene coated with hydrophilic impregnants and layers, such as described in U.S. Pat. No. 4,194,041. Alternatively, microporous polyolefin films or scrims which may be coated with or impregnated with hydrophilic polymers such as certain polyurethanes are also suitable for this use. The term "polyolefin" as used herein includes both halogen-free and halogenated polyolefins, e.g., polypropylene or polytetrafluoroethylene.

There are many benefits of using a waterproof, breathable orthopedic cast padded liner. The products of this invention allow cast or brace wearers to shower or swim while being immobilized without special precautions or drying procedures. This is advantageous not only for hygenic purposes, but also for various therapeutic reasons. Odor and itching can be reduced for cast patients if washing is allowed on a normal schedule. Cast wearers can engage in activities which may cause perfuse perspiration without the discomfort of wet underpadding. Use of hydrotherapy could aid in the healing process, as it does for some other injuries which do not require immobilization.

The breathable composites of this invention can be applied in a wrap formation similar to traditional cast underpaddings, or they can be configured to fit around the damaged limb in a single layer. The thinness of the film is essential to avoid bulky folds which can cause pressure sores on the skin.

Many athletes require the use of supportive braces to continue their training. Use of this padding would prevent perspiration from being trapped next to the skin following exertion. Alternatively, this padding could be incorporated directly into the brace.

The breathable quilted composites are also useful as thermal insulation in wearing apparel.

WATER VAPOR TRASMISSION RATE

Water vapor transmission rate was determined by ASTM 96-8 inverted cup method at 23°±1° C., at 50% relative humidity with a wind velocity of 500–600 FPM.

EXAMPLE

A porous, expanded polytetrafluoroethylene sheet was joined with a hydrophilic polymer, 9 inches wide and 4 yards long, as disclosed in U.S. Pat. No. 4,194,041, and was laid down on a flat rubbermat, hydrophilic side up. A 4 inch wide strip of polyester padding was laid on top. The two-member sheet was folded over the padding. A sealing iron at approximately 270° C. was used to make a seam down the open edge, enclosing the padding within the two-member sheet. The excess two-member sheet was trimmed, excess air was voided, and the ends were sealed. The resultant padded liner was worn under a polyurethane-coated fiberglass cast. The wearer showered daily, swam and used hydrotherapy on several occasions. No skin maceration was noted after an extended trial. No water leakage occured into the padding.

While the invention has been disclosed herein in connection with certain embodiments and detailed descriptions, it will be clear to one skilled in the art that modifications or variations of such details can be made without deviating from the gist of this invention, and such modifications or variations are considered to be with the scope of the claims hereinbelow.

What is claimed is:

1. A flexible, breathable, non-linting, composite comprising:
   (i) a middle layer of padding, and
   (ii) a top and bottom layer each comprising water impermeable and moisture-vapor-permeable porous film, said top and bottom layers encapsulating said middle layer by sealing the open edges of the top and bottom layers.

2. The composite of claim 1 wherein said top and bottom layers each comprise:
   (i) a flexible, water-impermeable, moisture-vapor-permeable, porous film as the external surfaces, and
   (iii) a continuous hydrophilic layer joined to the film said hydrophilic layer having a moisture vapor transmission rate exceeding 1000 gms./m$^2$·day and forming a barrier to passage of liquids wherein the layer (ii) is adjacent to said padding.

3. The composite of claim 1 wherein the porous film is porous, expanded polytetrafluoroethylene 4. The composite of claim 2 wherein the water-impermeable, moisture-vapor-permeable porous film is porous, expanded polytetrafluoroethylene and the hydrophilic layer is a polyurethane.

5. The composite of claim 1 or 2 wherein said middle layer is cotton.

6. The composite of claim 1 or 2 wherein said middle layer is foam.

7. The composite of claim 1 or 2 wherein said middle layer is polyester.

8. The composite of claim 1 or 2 wherein said middle layer is wool.

9. The composite of claim 1 or 2 in which the top and bottom layers of porous film define discrete quilt patterns in which the middle layer and top and bottom layers are compressed and bonded along the peripheral boundries of the quilt pattern.

10. Wearing apparel containing the composite laminate of claim 9.

11. Thermal insulation containing the composite laminate of claim 9.

12. An orthopedic immobilizer containing the composite of claim 1.

* * * * *